United States Patent [19]
DeLuca et al.

[11] Patent Number: 5,891,865
[45] Date of Patent: *Apr. 6, 1999

[54] TREATMENT OF ARTHRITIC DISEASE INDUCED BY INFECTIOUS AGENTS

[75] Inventors: Hector F. DeLuca, Deerfield; Margherita T. Cantorna, Middleton; Colleen E. Hayes, Madison, all of Wis.

[73] Assignee: Wisconsin Alumni Research Foundation, Madison, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 726,894

[22] Filed: Oct. 4, 1996

[51] Int. Cl.$^6$ ............................ A61K 31/59; C07J 175/00
[52] U.S. Cl. ............................................ 514/167; 552/653
[58] Field of Search ...................... 514/168, 167

[56] References Cited

U.S. PATENT DOCUMENTS

| | | | |
|---|---|---|---|
| 4,749,710 | 6/1988 | Truitt et al. | 514/167 |
| 4,857,518 | 8/1989 | DeLuca et al. | 514/167 |
| 5,098,899 | 3/1992 | Gilbert et al. | 514/167 |

FOREIGN PATENT DOCUMENTS

| | | |
|---|---|---|
| 0 387 077 A1 | 3/1990 | European Pat. Off. . |
| 0 579 915 A1 | 5/1993 | European Pat. Off. . |
| WO 86/02078 | 4/1986 | WIPO . |

OTHER PUBLICATIONS

M.M. André, et al., "Tenidap Inhibits T–cell Proliferation and Cytokine Production,." Sep. 1992, (Abstract).

A.K. Bhalla, et al., "1.25–Dihydroxyvitamin $D_3$ inhibits Lymphocyte Proliferation and Interleukin 2 Production: A Potential New Immunosuppressant," 1985 (Abstract).

E. Borba, et al., "Lipoprotein (a) Level is Increased in Systemic Lupus Erythematosus," Sep. 1992 (Abstract).

M.T. Cantorna, et al., "1,25–Dihydroxyvitamin $D_3$ Prevents and Ameliorates Symptoms in Two Experimental Models of Human Arthritis," Jan. 1997 (Abstract).

U.N. Das, "Interaction(s) Between Essential Fatty Acids, Eicosanoids, Cytokines, Growth Factors and Free Radicals: Relevance to New Therapeutic Strategies in Rheumatoid Arthritis and Other Collagen Vascular Diseases," *Prostaglandins, Leukotrienes and Essential Fatty Acids* 44 (4):201–210, 1991.

R.M. Flipo, et al., "Natural course of eroise arthropathy of the hands in dialized patients," Sep. 1992 (Abstract).

P. Goupille and J. –P. Valat, "Le Traitement du rhumatisme psoriasique," *Ann. Med. Interne.* 145 (3) :205–214, 1994.

R.A. Greenwald, et al., "Metalloproteinase (MMP) Activity and Radiologic Severity of Adjuvant Arthritis (AA) : Synergistic Beneficial Effects of Tenidap 9TD) and 4–dedimethylaminotetracycline (CMT) ," Sep. 1992 (Abstract).

M.E. Hayes, et al., "Synthesis of the active metabolite of vitamin D, 1,25 $(OH)_2D_3$, by synovial fluid macrophages in arthritic diseases," *Ann. Rheum. Dis.* 48 : 723–729, 1989.

M.F. Holick, "Noncalcemic Actions of 1,25–Dihydroxyvitamin $D_3$ and Clinical Applications," *Bone* 17 (2):107S–111S, 1995.

D. Huckins, et al., "Treatment of Psoriatic Arthritis with Oral 1,25–Dihydroxyvitamin $D_3$ : A Pilot Study,"*Arth. Rheum.* 33 (11) :1723–1727, 1990.

J. Martel–Pelletier, et al., "Tenidap, a New Anti–rheumatic Drug, Reduced IL–1R Expression and IL–1–induced Expression of Metalloproteases in Cartilage Human Chondrocytes," Sep. 1992 (Abstract).

K. Müller and K. Bendtzen, Inhibition of Human T Lymphocyte Proliferation and Cytokine Production by 1,25–Dihydroxivitamin $D_3$. Differential Effects on CD45RA+ and CD45RO+ Cells, *Autoimmunity* 14:37–43, 1992.

M.H. Pioro and J.M. Cash, "Treatment of Refractory Psoriatic Arthritis," *Rheumatic Disease Clinics of North America* 21 (1) :129–149, 1995.

A. Raj, et al., "Evidence for Local Synthesis of 1,25–dihydroxyvitamin D in the Synovial Compartment of the Joint in Pitentis with Inflammatory Arthritis," Sep. 1992 (Abstract).

F. Shapiro, "Osteopetrosis,"*Clin. Ortho. Rel. Res.* 294 : 34–44, 1993.

S. Yang, et al., "1α25–dihydroxyvitamin $D_3$ and 19–nor–1α, 25–dihydroxyvitamin $D_2$ suppress immunoglobulin production and thymic lymphocyte proliferation in vivo," *Biochemica et Biophysica Acta* 1158: 279–286, 1993.

*Primary Examiner*—Theodore J. Criares
*Attorney, Agent, or Firm*—Quarles & Brady

[57] ABSTRACT

A method of treating arthritis symptoms induced by an infectious agent of an arthritis patient comprising administering to an arthritis patient an amount of vitamin D compound effective to reduce symptoms and observing a reduction in symptoms is disclosed.

14 Claims, 2 Drawing Sheets

TREATMENT OF ARTHRITIC DISEASE INDUCED BY INFECTIOUS AGENTS

This invention was made with United States government support warded by NIH, Grant No. DK14881. The United States Government has certain rights in this invention.

FIELD OF THE INVENTION

In general, the field of the present invention is treatment of arthritic disease. Specifically, the field of the present invention is treatment of arthritic disease with vitamin D analogs.

BACKGROUND

Arthritic Disease

One of the most intensively studied arthritic diseases is rheumatoid arthritis. There is a major genetic contribution for the predisposition to rheumatoid arthritis. People who inherit a group of defined HLA major histocompatibility complexes account for 90% of the rheumatoid arthritis patients (Winchester, R., *Adv. Immunol.* 56:389–466, 1994). Rheumatoid arthritis is a chronic and destructive disease that primarily affects the joints of the extremities and is characterized by inflammation of the synovium and destruction of joint structural components. The symptoms and morphology suggest a local immune response. Both cell-mediated and humoral immune responses may contribute to development of lesions (Abbas, et al., *Cellular and Molecular Immunology*, Ch. 20, W. B. Saunders Co., Philadelphia, 1990).

Numerous cytokines have been detected in the synovial (joint) fluid of arthritic patients, and these cytokines are believed to activate resident synovial cells to produce hydrolytic enzymes (e.g., collagenase and matrix metalloproteinase) that mediate the destruction of the cartilage.

The etiology of rheumatoid arthritis is unknown. It is likely that many different causes trigger the development of what is diagnosed as rheumatoid arthritis. There are bacterial infections which are known to result in the development of arthritis. These would include arthritis which results from infections with Borrelia, Yersinia, Salmonella, Shigella, Campylobacter or Chlamydia species. Regardless of the cause, once the joint becomes inflamed there is a well documented immune mediated attack on one of the major structural components of the joints, collagen (Trentham, D. E., et al., *J. Exp. Med.* 146:857–868, 1977).

There are several experimental animal models of arthritis. Collagen injections in mice, rats and primates result in the development of arthritis. The best studied animal model is collagen-induced arthritis in DBA/1 mice. Arthritic disease can also be induced in mice infected with *Borrelia burgdorferi*, the causative agent of Lyme arthritis.

Current treatment regimes for rheumatoid arthritis include symptomatic drugs in combination with disease-modifying drugs (Machold, K. P., et al., *Annals Rheum. Dis.* 51:1039–1043, 1992). Disease modifying drugs include gold salts, D-Penicillamine, hydroxychloroquine, and cytostatic drugs which have limited efficacy and significant toxicity. Arthritic diseases caused by infectious agents, such as *Borrelia burgdorferi*, are treated with symptomatic drugs in combination with antimicrobial therapy (Steere, A. C., *N. Engl. J. Med.*, 321:586–596, 1989). Regardless of the cause, symptomatic treatment of arthritis is uniformly steroid therapy.

Arthritic disease can also be caused by infectious agents such as *Borrelia burgdorferi*, which causes Lyme disease. Current methods of treating Lyme arthritis include symptomatic drugs in combination with antimicrobial therapy to eradicate the spirochete.

$1,25(OH)_2D_3$ and Analogs

The $1\alpha$-hydroxylated metabolites of vitamin D-most importantly $1\alpha,25$-dihydroxyvitamin $D_3$ and $1\alpha,25$-dihydroxyvitamin $D_2$—are known as highly potent regulators of calcium homeostasis in animals and humans. More recently, their activity in cellular differentiation has also been established. As a consequence, many structural analogs of these metabolites, such as compounds with different side-chain structures, different hydroxylation patterns, or different stereochemistry, have been prepared and tested. Important examples of such analogs are $1\alpha$-hydroxyvitamin $D_3$, $1\alpha$-hydroxyvitamin $D_2$, various side-chain fluorinated derivatives of $1\alpha,25$-dihydroxyvitamin $D_3$, and side-chain homologated analogs. Several of these known compounds exhibit highly potent activity in vivo or in vitro, and possess advantageous activity profiles and thus are in use, or have been proposed for use, in the treatment of a variety of diseases such as renal osteodystrophy, vitamin D-resistant rickets, osteoporosis, psoriasis, multiple sclerosis, and certain malignancies.

1,25-Dihydroxyvitamin $D_3$ As An Immunomodulator

The first indication that vitamin D might modulate immunity was the discovery that peripheral blood monocytes and activated T lymphocytes have 1,25-dihydroxyvitamin $D_3$ receptors (reviewed in Manolagas, S. C., et al. *Mol. and Cell. Endocrin.* 43:113–122, 1985). Despite many investigations, 1,25-dihydroxyvitamin $D_3$ immunomodulatory activity remains largely undefined and often controversial (reviewed in Manolagas, S. C., et al., supra, 1985; Rigby, W. F. C., *Today* 9:54–57, 1988; and Lemire, J. M., et al., *J. Nutr.* 125:1704S–1708S, 1995).

The action of 1,25-dihydroxyvitamin $D_3$ on human peripheral blood mononuclear cells (PBMC) has been studied extensively in vitro. These in vitro experiments showed that the hormone inhibited mitogen-stimulated proliferation of the PBMC (Lemire, J. M., et al., *J. Clin Invest.* 74:657–661, 1984; Rigby, W. F. C., et al., *J. Clin. Invest.* 74:1451–1455, 1984) by reducing IL-2 production (Lemire, J. M., et al., *J. Immunol.* 134:3032, 1985; Iho, S., et al., *Immunol. Let.* 11:331–336, 1985; Manolagas, S. C., et al.,*J. Clin. Endocrinol. Met.* 63:394, 1986) at the level of gene transcription (Alroy, I., et al.,*Mol. Cell. Biol.* 15:5789–5799, 1995). In contrast, Bhalla, et al. (Bhalla, A. K., et al., *J. Immunol.* 133:1748–54, 1984) reported that the hormone did not inhibit mitogen-stimulated mouse spleen and thymus cell proliferation, although it did inhibit antigen-stimulated proliferation of these cells. Lacey, et al. (Lacey, D. L., et al., *J. Immunol.* 138:1680–1686, 1987) reported that the hormone actually stimulated mitogen-induced proliferation of cloned mouse T-cells. No studies have directly addressed the action of the hormone on T lymphocyte differentiation and function in vivo.

Disparate results have been reported for T lymphocyte IFN-γ synthesis in vitro. Rigby, et al. (Rigby, W. F. C., et al., *J. Clin. Invest.* 79:1659–1664, 1987) and Reichel, et al. (Reichel, H., et al., *Proc. Natl. Acad. Sci. USA* 84:3387–3389, 1987) showed that 1,25-dihydroxyvitamin $D_3$ decreased IFN-γ synthesis in mitogen-stimulated PBMC. However, Muller, et al. (Muller, K., et al. *Immunol. Let.* 35:177–182, 1993) reported that the hormone had no effect on IFN-γ synthesis in human T-cell lines. The hormone inhibited cytotoxic T lymphocyte development but not cytotoxic function (Merino, F., et al., *Cell. Immunol.* 118:328–336, 1989).

There is controversy about 1,25-dihydroxyvitamin $D_3$ action on monocyte/macrophage cells in vitro. 1,25-Dihydroxyvitamin $D_3$ enhanced a myeloid leukemia cell's differentiation to the macrophage phenotype (Manolagas, S. C., et al., supra, 1985). It also increased monocyte/macrophage production of M-CSF, TNF-α, and prostaglandin E2, but decreased IL-12 synthesis (Lemire, J. M., et al., *FASEB J.* 8:A745 (abs), 1994). The hormone decreased macrophage costimulatory function for T-cell proliferation (Rigby, W. F. C. and M. G. Waugh, *Arthritis Rheum.* 35:110–119, 1992). Disparate results have been reported for 1,25-dihydroxyvitamin $D_3$ effects on IL-1 synthesis in vitro. The hormone decreased IL-1 synthesis in some reports (Iho, S., et al., supra, 1985; Tsoukas, C. S., et al., *J. Clin. Endocrinol. Metab.* 69:127–133, 1989) and increased IL-1 synthesis in other reports (Amento, E. P., *J. Clin. Invest.* 73:731–739, 1987; Bhalla, A. K., et al., *Immunol.* 72:61–64, 1991; Fagan, D. L., et al., *Mol. Endocrinol.* 5:179–186, 1991). Likewise, some investigators reported that 1,25-dihydroxyvitamin $D_3$ enhanced class II protein expression in vitro (Morel, P. A., et al., *J. Immunol.* 136:2181–2186, 1986) but others reported that it decreased class II protein expression (Amento, E. P., supra, 1987; Carrington, M. N., et al., *J. Immunol.* 140:4013–4018, 1988; Rigby, W. F. C., et al., *Blood* 76:189–197, 1990). Together these findings provide no clear and consistent view of how 1,25-dihydroxyvitamin $D_3$ might modify macrophage function. No studies have directly addressed the action of the hormone on monocyte/macrophage differentiation and function in vivo.

There is also controversy about 1,25-dihydroxyvitamin $D_3$ action on B lymphocytes (reviewed in Rigby, W. F. C., supra, 1988). Lemire, et al. (Lemire, J. M., et al., supra, 1984) reported that the hormone inhibited mitogen-stimulated $I_gG$ and $I_gM$ synthesis by human peripheral blood mononuclear cells. Suppressive and enhancing effects of 1,25-dihydroxyvitamin $D_3$ on mitogen-stimulated B cell proliferation and on antibody synthesis in vitro have been shown. In vivo, 1,25-dihydroxyvitamin $D_3$ has been reported to enhance antibody synthesis in some studies (Abe, J., et al., *Endocrinology* 124:2645–2647, 1989; Ross, T. K., et al., *Vitamins Hormones* 49:281–326, 1994; Daynes, R. A., et al., *Infec. Immun.* 64:1100–1109, 1996) and to inhibit it in other studies (Lemire, J. M., et al., supra, 1995).

There is a great deal of interest in arthritis treatments. Present drug treatments for arthritis include non-steroidal anti-inflammatory drugs (see Paulus, H. E. and D. E. Furst, *Arthritis and Allied Conditions in A Textbook of Rheumatology*, D. J. McCarty, Ed., Lea & Febiger, Philadelphia, Pa., pp. 507–543, 1989) such as naproxen, piroxicam, indomethacin, sulindac, aspirin, salicylsalicyclic acid, sodium meclofenamate, diflunisal, tolmetin, phenylbutazone, oxyphenbutazone, ibuprofen, fenoprofen, ketoprofen; disease-modifying antirheumatic drugs such as chloroquine, hydroxychloroquine, D-penicillamine, auranofin, aurothiomalate, methotrexate, azathioprine, sulphasalazine; and steroidal anti-inflammatory drugs such as corticosteroids (see McCarty, D. J., *Arthritis and Allied Conditions. A Textbook of Rheumatology*, Lea & Febiger, Philadelphia, Pa., pp. 659–782, 905–990, 1989).

The American College of Rheumatology and the International League Against Rheumatism published a core set of rheumatoid arthritis outcome measures to be used in clinical trials (Felson, D. T., et al., *Arthritis Rheumatol.* 36:729–740, 1993). These outcome measures include:

1. Progression in physical parameters such as number of joints that are painful, number of joints that are swollen, and both patient and physician global opinion of rheumatoid arthritis activity.
2. An assessment of joint physical function like angle of joint deformity, limited joint motion, and decreased functional capacity as described by Young, et al. (Young, A. M., et al. *Br. J. Rheumatol.* 27:94–101, 1988) and McCarty, et al. (supra, 1989) and measured with the Health Assessment Questionnaire (Felson, D. T., et al., supra, 1993).
3. Pain
4. Laboratory measures of the inflammatory acute phase reaction like C-reactive protein as described by van Leeuwen, et al. (van Leeuwen, M., et al. *Arthritis Rheum.* 37(suppl. 9):S331, 1994).
5. Radiographic progression in serial radiographs taken over ≦1 year of the wrists, hands, and feet, scored as described by Sharp (Sharp, J. T., Scoring radiographic abnormalities in rheumatoid arthritis. In: *Radiologic Clinics of North America* 34(2):233–241, 1996), Wilhelm, et al. (Wilhelm, F. E., et al., *Arthritis Rheum.* 37(suppl.):S336, 1994), Nance, et al. (Nance, E. P., et al., *Invest. Radiol.* 21:922–927, 1986), or some similarly quantitative method.

Improvement has been defined (Felson, D. T., et al., supra, 1993) as a ≦20% improvement in painful/tender joint counts and in swollen joint counts, and ≦20% improvement in at least three of the other criteria (patient opinion, physician opinion, physical function, pain index, or acute phase reactant).

A new drug category, disease-controlling antirheumatic therapy (D-CART), was recently defined (Edmonds, J. P., *J. Rheumatol.* 21(suppl.41):1–63, 1994). To qualify for D-CART status, a therapy must produce a sustained improvement in physical function, a decrease in inflammatory synovitis, and a slowing or halting of progressive structural joint damage as documented by serial radiographs or other imaging studies.

Needed in the art is an improved arthritis treatment method.

SUMMARY OF THE INVENTION

The present invention is a method of preventing arthritis in susceptible individuals and treating arthritis patients by administering an amount of a vitamin D compound, preferably 1,25(OH)$_2$D$_3$ or analogs thereof, effective to prevent arthritis development or to diminish the arthritis symptoms, respectively. The method comprises selecting an arthritis patient and administering a sufficient amount of the vitamin D analog to the patient such that the arthritis symptoms are abated.

In a particularly advantageous form of the reaction, the administered compound is either 1α,25-dihydroxyvitamin D$_3$ (1,25-(OH)$_2$D$_3$), 19-nor-1,25-dihydroxyvitamin D$_2$ (19-nor-1,25-(OH)$_2$D$_3$), 24-homo-22-dehydro-22E-1α,25-dihydroxyvitamin D$_3$ (24-homo-22-dehydro-22E-1,25-(OH)$_2$D$_3$), 1,25-dihydroxy-24(E)-dehydro-24-homo-vitamin D$_3$ (1,25-(OH)$_2$-24-homo D$_3$), or 19-nor-1,25-dihydroxy-21-epi-vitamin D$_3$ (19-nor-1,25-(OH)$_2$-21-epi-D$_3$). In a most preferred form of the invention, the compound is 1,25(OH)$_2$D$_3$.

A preferred dose of vitamin D compound for the present invention is the maximum that a patient can tolerate and not develop serious hypercalcemia.

If the vitamin D compound is not a 1α-hydroxy compound, a particularly advantageous daily dose of vitamin D compound is between 5.0 and 50 μg per day per 160 pound patient. If the vitamin D compound is a 1α-hydroxy compound, the preferred dose is between 0.5 and 10 μg per day per 160 pound patient. If the patient has calcium intakes of above 800 mg/day, doses of 1,25(OH)$_2$D$_3$ over 0.75 µg per day per 160 pound patient are not preferred. If the patient is on a low calcium diet and/or takes the dose late at night, higher doses of 1,25(OH)$_2$D$_3$ would be possible and would be preferred. In this embodiment of the invention, the amount of 1,25(OH)$_2$D$_3$ administered could be as high as 1.5 µg per day per 160 pound patient. A preferred dose would be 0.5–1.0 µg per day per 160 pound patient.

It is an advantage of the present invention that the method diminishes arthritis symptoms.

It is another advantage of the present invention that the method diminishes arthritis onset.

It is an advantage of the present invention that susceptible individuals can be prophylactically treated to prevent the development of arthritis.

Other advantages and features of the present invention will become apparent after examination of the specification, claims and drawings.

DESCRIPTION OF THE DRAWINGS

FIG. 4A graphs the measurement of ankle size.

DESCRIPTION OF THE INVENTION

Figure 1:
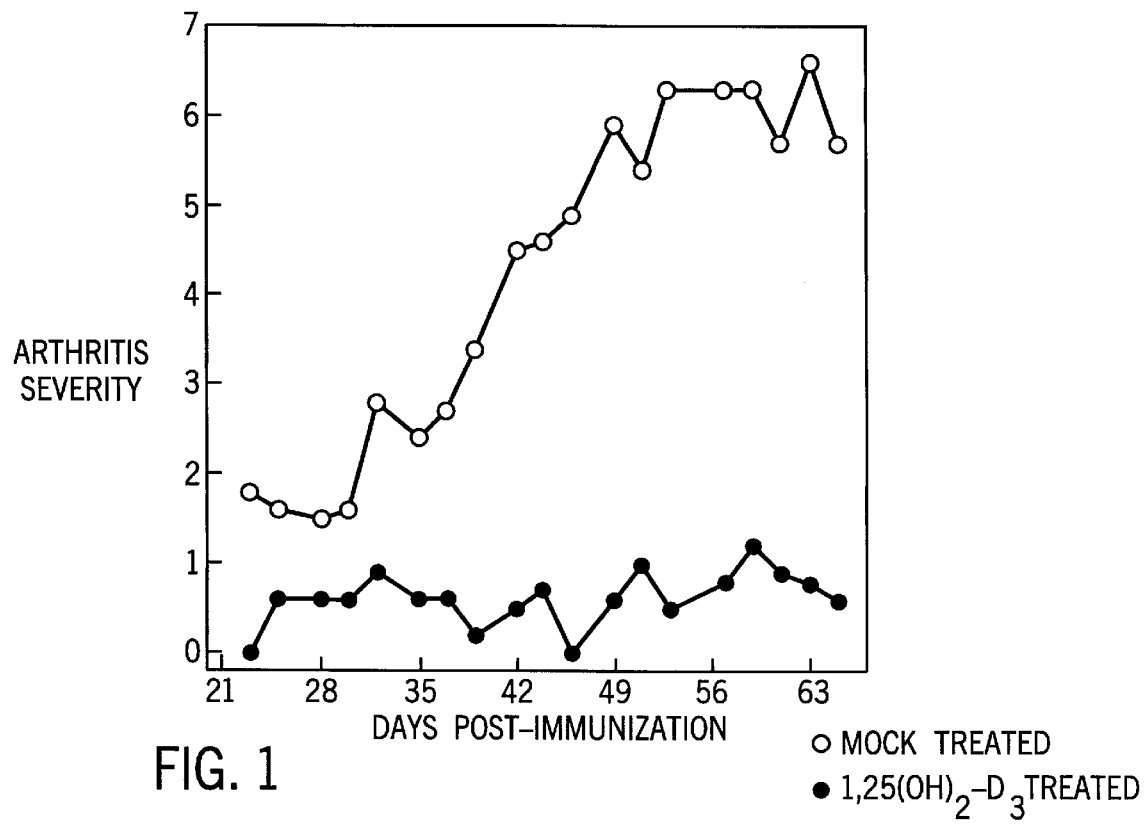
FIG. 1 is a graph of arthritis severity in mock-treated and 1,25(OH)$_2$D$_3$-treated DBA/1 mice versus days post-immunization.

The present invention is a method of treating human arthritis patients by administering an amount of a vitamin D compound, preferably 1,25(OH)$_2$D$_3$ or analogs thereof, effective to diminish the arthritis symptoms. The method comprises selecting an arthritis patient and administering a sufficient amount of the vitamin D analog to the patient such that the arthritis symptoms are abated.

In a particularly advantageous form of the reaction, the administered compound is either 1α,25-dihydroxyvitamin D$_3$ (1,25-(OH)$_2$D$_3$), 19-nor-1,25-dihydroxyvitamin D$_2$ (19-nor-1,25-(OH)$_2$D$_2$), 24-homo-22-dehydro-22E-1α,25-dihydroxyvitamin D$_3$ (24-homo-22-dehydro-22E-1,25-(OH)$_2$D$_3$), 1,25-dihydroxy-24(E)-dehydro-24-homo-vitamin D$_3$ (1,25-(OH)$_2$-24-homo D$_3$), or 19-nor-1,25-dihydroxy-21-epi-vitamin D$_3$ (19-nor-1,25-(OH)$_2$-21-epi-D$_3$).

In another form of the present invention, the vitamin D compound has the formula

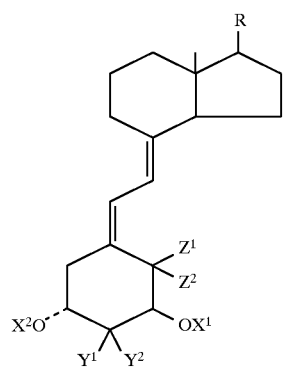

wherein X$^1$ and X$^2$ are each selected from the group consisting of hydrogen and acyl;

wherein Y$^1$ and Y$^2$ can be H, or one can be O=aryl or O=alkyl and can have a β or α configuration; Z$^1$=Z$^2$=H or Z$^1$ and Z$^2$ together are CH$_2$; and wherein R is an alkyl, hydroxyalkyl or fluoroalkyl group, or R may represent the following side chain:

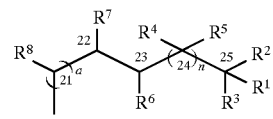

wherein (a) may have an S or R configuration, R$^1$ represents hydrogen, hydroxy or O-acyl, R$^2$ and R$^3$ are each selected from the group consisting of alkyl, hydroxyalkyl and fluoralkyl, or, when taken together represent the group —(CH$_2$)$_m$— wherein m is an integer having a value of from 2 to 5, R$^4$ is selected from the group consisting of hydrogen, hydroxy, fluorine, O-acyl, alkyl, hydroxyalkyl and fluoralkyl, wherein if R$^5$ is hydroxyl or fluoro, R$^4$ must be hydrogen or alkyl, R$^5$ is selected from the group consisting of hydrogen, hydroxy, fluorine, alkyl, hydroxyalkyl and fluoroalkyl, or R$^4$ and R$^5$ taken together represent double-bonded oxygen, R$^6$ and R$^7$ taken together form a carbon-carbon double bond, R$^8$ may be H or CH$_3$, and wherein n is an integer having a value of from 1 to 5, and wherein the carbon at any one of positions 20, 22, or 23 in the side chain may be replaced by an O, S, or N atom.

One may evaluate a candidate vitamin D compound for its suitability for the present invention. The candidate compound should first be subjected to an initial mouse-model screening procedure, such as that described below for 1,25-(OH)$_2$D$_3$ in the Examples below. A successful compound will reduce arthritic symptoms in DBA/1 mice, preferably to the extent shown in the Examples for 1,25-(OH)$_2$D$_3$. However, a successful compound is generally described as one that reduces arthritic symptoms. Preferably, the compound should show a significant reduction in lesions. The compound would then be predicted to be successful in human patients.

A preferred dose of vitamin D compound for the present invention is the maximum that a patient can tolerate and not develop serious hypercalcemia.

If the vitamin D compound is not a 1α-hydroxy compound, a particularly advantageous daily dose of vitamin D compound is between 5.0 and 50 µg per day per 160 pound patient.

If the vitamin D compound is a 1α-hydroxy compound, the preferred dose is between 0.5 and 10 μg per day per 160 pound patient. If the patient has normal calcium intakes, doses of a 1α-hydroxy compound, such as 1,25(OH)$_2$D$_3$, over 0.75 μg per day per 160 pound patient are not preferred. If the patient is on a low calcium diet and/or takes the dose late at night, higher doses of 1,25(OH)$_2$D$_3$ would be possible and would be preferred. In this embodiment of the invention, the amount of 1,25(OH)$_2$D$_3$ administered could be as high as 1.5 μg per day per 160 pound patient. A preferred dose would be 0.5–1.5 μg per day per 160 pound patient.

1,25-dihydroxyvitamin D$_3$ (1,25-(OH)$_2$D$_3$) is currently administered at a level of 0.5 μg/day per 160 pound patient, usually in two quarter microgram capsules morning and night for the treatment of osteoporosis or renal osteodystrophy. In countries where dietary calcium is of the order of 800 mg/day or even up to 1,000 mg/day, higher doses of 1,25-(OH)$_2$D$_3$ cannot be used because the dose results in increased urinary calcium and increased plasma calcium with the danger of hypercalcemia and resultant deterioration of the kidney, calcification of the heart, lung, aorta, and other soft tissues.

Therefore, the maximum preferred dose of 1,25-(OH)$_2$D$_3$ would appear to be at 0.5 μg/day. However, higher doses can be used under circumstances when dietary calcium is of the order of 600 mg/day. Other less active 1α-hydroxy vitamin D compounds can be given at higher doses safely. For example, in Japan the treatment of osteoporosis with 1,25-(OH)$_2$D$_3$ is 0.5 to 0.75 μg/day. The same is true of other low calcium countries, such as Italy, where as much as 1 mg/day of 1,25-(OH)$_2$D$_3$ has been successfully used by Dr. Caniggia (Caniggia, A., et al., *Metabolism* 39:43–49, 1990).

We also envision a lower preventative dose in susceptible people with or without modification of calcium.

We believe that for the treatment of arthritic disease, higher dose of 1,25-(OH)$_2$D$_3$ would be most helpful. Calcium intake can be reduced to approximately 400–500 mg/day by merely eliminating dairy products and calcium supplements from the diet. Furthermore, the dose of 1,25-(OH)$_2$D$_3$ can be given at night before bedtime, i.e. 10 p.m., and because of the time of appearance of this compound in the circulation, calcium absorption would be at a minimum, allowing for larger doses of 1,25-(OH)$_2$D$_3$.

A preferred treatment regime would be the following: Reduce the patient's calcium intake to about 500 mg/day by eliminating all supplements of calcium and also reducing the consumption of dairy products, providing for a dietary intake of calcium of 500 mg. If, under these circumstances, the 1,25-(OH)$_2$D$_3$ is also administered at 10 p.m., the dose of 1,25-(OH)$_2$D$_3$ can be safely increased to up to 1 μg or perhaps 2.0 μg/day.

The preferred mode of treatment for 1α-hydroxy compounds is administration under regular dietary circumstances of 0.5–0.75 μg/day of the compound. A preferred method would be to administer 0.75–1 μg/day at 10 p.m. or before bedtime. A most preferred method would be to both reduce the dietary calcium intake to 400–500 μg/day and to administer between 0.75 and 1.5 μg/day at 10 p.m.

A preferred mode of treatment for non-1α-hydroxy compounds would also be administration under regular dietary circumstances. In this case, the treatment dose could be increased up to 50 μg/day per 160 pound patient.

An optimum treatment dose will be determined upon observation of reduction of an arthritis patient's symptoms as a function of the amount of vitamin D compound administered.

By "arthritic disease" we mean disease symptoms characterized by inflammatory synovitis accompanied by overt physical signs like joint pain, joint redness, joint swelling, limited joint motion, joint deformity, decreased joint strength (for example, in a grip test) and decreased joint dexterity (for example, in a button test). Additional symptoms include cartilage, tendon, ligament and/or bone erosion and a narrowing of joint spacing as depicted radiographically or by some other imaging method.

Arthritic disease includes the arthritis symptoms of unknown etiology such as rheumatoid arthritis and the arthritis symptoms induced by infectious agents, including but not limited to, Lyme arthritis. Specifically included are inflammatory arthritic diseases such as rheumatoid arthritis, juvenile rheumatoid arthritis, seronegative polyarthritis, ankylosing spondylitis, Reiter's syndrome: reactive arthritis, psoriatic arthritis, and enteropathic arthritis.

By a "reduction in arthritic symptoms" we mean a $\leq 20\%$ decrease in the number of painful joints, a $\leq 20\%$ decrease in the number of swollen joints, and a $\leq 20\%$ improvement in three additional measures of arthritis severity including range of joint motion, joint strength, joint dexterity and/or inflammatory acute phase C-reactive protein (Felson, et al., supra, 1993; van Leeuwen, et al., supra, 1994). In the ideal case (Edmonds, supra, 1994), abatement of symptoms would lead to a controlling of the disease process as measured by a sustained ($\leq 1$ year) improvement in physical function, a decrease in inflammatory synovitis and a slowing or halting of progressive structural joint damage as documented by serial radiographs or other imaging studies scored as described by Sharp (supra, 1996), Wilhelm, et al. (supra, 1994), Nance, et al. (supra, 1986) or some similarly quantitative method.

The method of the present invention is also useful for delaying or preventing the onset of arthritis in susceptible individuals.

Susceptible individuals are people with an affected family member (i.e., by direct descent) or any person known to carry a susceptible HLA haplotype such HLA-DR4 or HLA-DR1 (see *Annual Review Immunology* 9:493, 1991).

The experiments below demonstrate a reduction in arthritis symptoms in model mice from severe redness and swelling to definite swelling to redness with some swelling to no symptoms. We predict a similar type of reduction of symptoms in human patients.

EXAMPLES

Materials and Methods

Treatments. Mice were split into groups of 8–12 mice; one group was fed the experimental diet alone, other groups were fed the experimental diet plus various concentrations of 1,25-dihydroxyvitamin D-3 (1,25-(OH)$_2$D$_3$). Experimental diets (Smith, S. M., et al., *J. Nutr.* 117:857, 1987) were made and replaced every 2–3 days for the duration of the experiment. At the end of the experiments mice were sacrificed, weighed, and bled for serum calcium analysis.

One experiment was done with a diet containing 2.2% CaCO$_3$ and the second experiment was done on a low calcium diet containg 0.2% CaCO$_3$. Normal mouse chow contained 1.2% CaCO$_3$.

Reagents. Bovine collagen, Type II was purchased from Elastin Products Company, Inc. (Owensville, Mo.). Collagen was dissolved in 0.1M acetic acid at a concentration of 4 mg/ml. Collagen was emulsified in an equal volume of complete Freund's adjuvant (CFA) containing mycobacterium tuberculosis H37 Ra (4 mg/ml).

Immunization. DBA/1 LacJ mice were purchased from Jackson Laboratories (Bar Harbor, ME). Ether-anesthetized male DBA/1 mice were immunized s.c. with 0.05 ml of collagen (100 μg/mouse) emulsified in CFA. In addition, twenty-one days later the mice were boosted (intraperitoneal injection) with 100 μg of collagen in sterile saline. This immunization protocol resulted in the induction of collagen-induced arthritis, an animal model of human arthritis.

Disease severity. Mice were scored daily using a standard scoring system for collagen-induced arthritis in mice (Wooley, P. H., et al. *J. Immunol.* 134:2366). Each of four paws was scored as follows: 0-no symptoms, 1-redness with some swelling, 2-definite swelling with some paw distortion, 3-difficulty using the paw with severe redness and swelling. The paw scores for all the mice were added and divided by the number of mice per treatment group. The maximum arthritis severity score is 12.

Figure 4A:
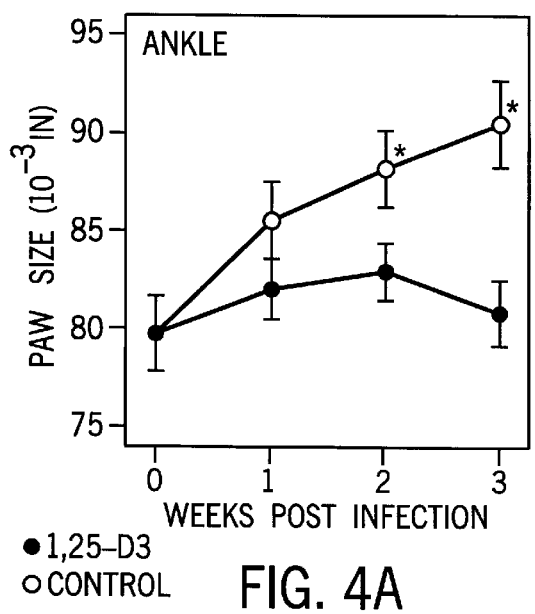
FIGS. 4A and B is a graph of paw size of 1,25-(OH)$_2$D$_3$-treated and mock-treated C3H/HeJ mice versus weeks post-infection with N40 strain spirochetes.
Figure 4B:
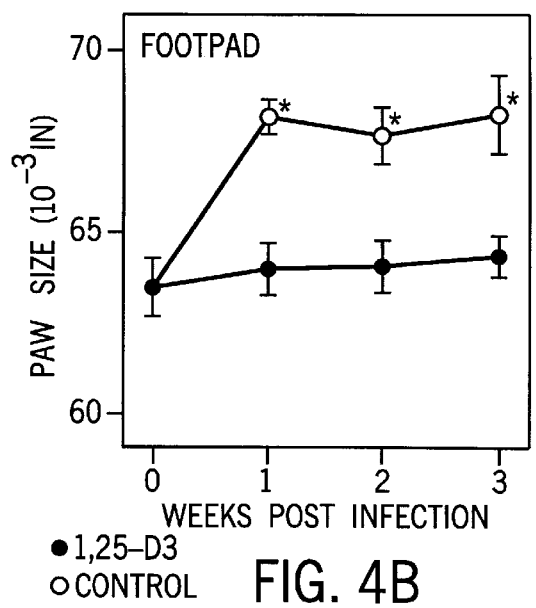
FIG. 4B graphs the measurement of footpad size.

*B. burgdorferi* and arthritis severity, FIG. 4. C3H/He mice were purchased from Sprague Dawley. Spirochetes were grown in BSK-II medium and enumerated as described (Barthold, S. W., et al., *J. Infect. Dis.* 162:133, 1990). Experiments used cloned *B. burgdorferi* strain N40 generously provided by Dr. S. W. Barthold (Yale University, School of Medicine, New Haven, Conn.).

Mice were injected intradermally with N40 strain spirochetes ($10^4$) in 0.1 ml of medium, or medium only. Bladder samples were collected and cultured for 2 weeks in BSK-II medium, and examined microscopically to confirm the infection. All of the mice were considered infected because the mice yielded *B. burgdorferi* positive cultures. Arthritis was quantitated by measuring changes in the ankle joint and footpads of ether-anesthetized mice (Barthold, S. W., et al., supra, 1990; Miller, L. C., et al., *J. Clin. Invest.* 90:906, 1992); ankle joint measurements correlate with the histological severity of arthritis in mice (Miller, L. C., et al., supra, 1992). Tissue sections were also prepared and these confirmed the arthritis (Miller, L. C., et al., supra, 1992).

Results

We first compared mock-treated mice and $1,25-(OH)_2D_3$-treated (20 ng/day) mice on a 2.2% $CaCO_3$ diet to compare severity scores during arthritis induction. A visual observation of the three mice shown on day 40 post-immunization indicated that the arthritis severity scores (as described above) averaged 10 and 6 for the mock-treated mice but 0 for the $1,25-(OH)_2D_3$-treated mice. As a whole, the 20 ng/day dose of $1,25(OH)_2D_3$ on a diet containing 2.2% $CaCO_3$ decreased the incidence of arthritis by 50% and the severity of arthritis from an average severity score of 5.5 to 2.5. The next experiment was done on a higher dose of $1,25(OH)_2D_3$ and a low calcium diet (0.2% $CaCO_3$) in order to increase the effectiveness of treatment and decrease the resulting calcium toxicity.

Our next set of experiments were designed to evaluate the effect of early $1,25-(OH)_2D_3$ treatment on arthritis severity. FIG. 1 graphs the result of this experiment.

Referring to FIG. 1, early $1,25-(OH)_2D_3$ treatment is shown to reduce the severity of collagen-induced arthritis in DBA/1 mice. The experimental diet contained either 50 ng/day/mouse $1,25-(OH)_2D_3$ or no additional D and was low in calcium. The experimental diet was started on day 14 post-immunization with collagen.

The paws were scored as before. The paw scores were added and divided by the number of mice per treatment as follows: 0-no symptoms, 1-redness with some swelling, 2-definite swelling with some paw distortion, 3-difficulty using the paw with severe redness and swelling. The maximum score is 12.

FIG. 1 demonstrates that arthritis severity is much reduced with $1,25(OH)_2D_3$ treatment versus untreated mice. The untreated mice had a high score of 6 at 49 days. Treated mice had a score of less than 1 throughout the experiment.

A mouse with a score of 6 is a mouse with at least one distorted paw and may not have the use of one or more paws. The treated mice had a score of 1 or less through the experiment. A mouse with a score of 1 might have one red paw but otherwise is healthy and moving with unrestricted movement.

Figure 2:
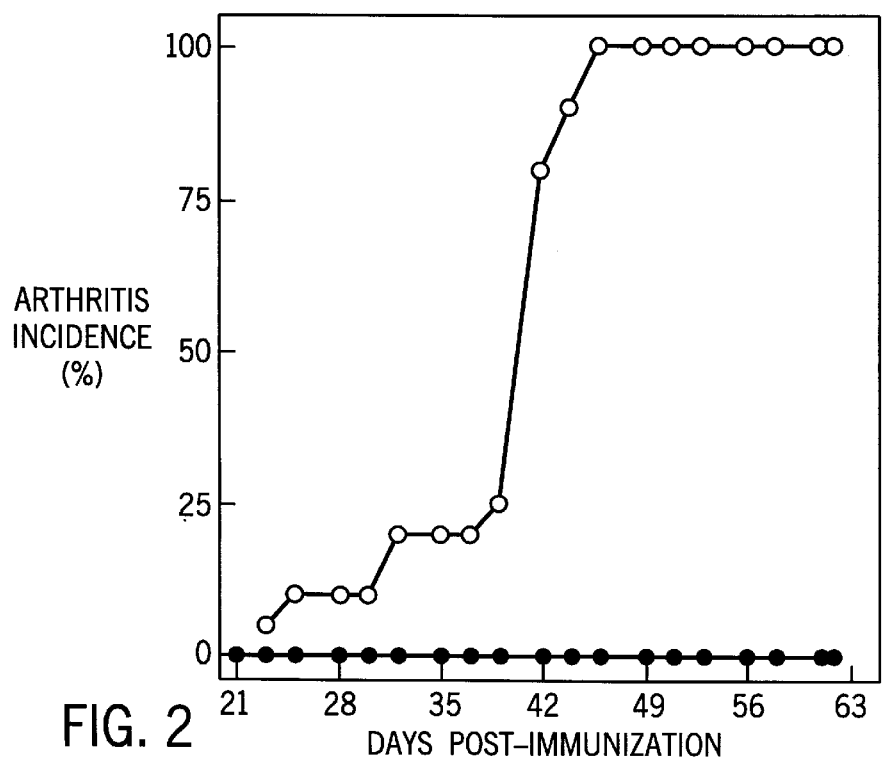
FIG. 2 is a graph of arthritis incidence (percentage) of mock-treated and 1,25-(OH)$_2$D$_3$-treated DBA/1 mice versus days post-immunization.

The next figure was derived from the same group of mice as FIG. 1. FIG. 2 graphed the incidence of arthritis versus the time post-immunization. Mice were not considered arthritic until one of their paws scored 2 or higher. FIG. 2 shows that beginning $1,25(OH)_2D_3$ treatment before the first arthritis symptoms prevents a mouse from developing arthritis.

The data in FIGS. 1 and 2 demonstrate that early $1,25-(OH)_2D_3$ treatment prevented collagen-induced arthritis in DBA/1 mice. The diet provided 50 ng/day $1,25-(OH)_2D_3$, contained 0.2% $CaCO_3$ and was started on day 14 post-immunization. Mice were not considered to be arthritic until one of four paws was scored as 2 or higher.

FIG. 2 shows that the $1,25-(OH)_2D_3$-treated mice did not develop collagen-induced arthritis for at least 64 days post-immunization with collagen. In contrast, the untreated mice had a 100% incidence of arthritis at 64 days.

Figure 3:
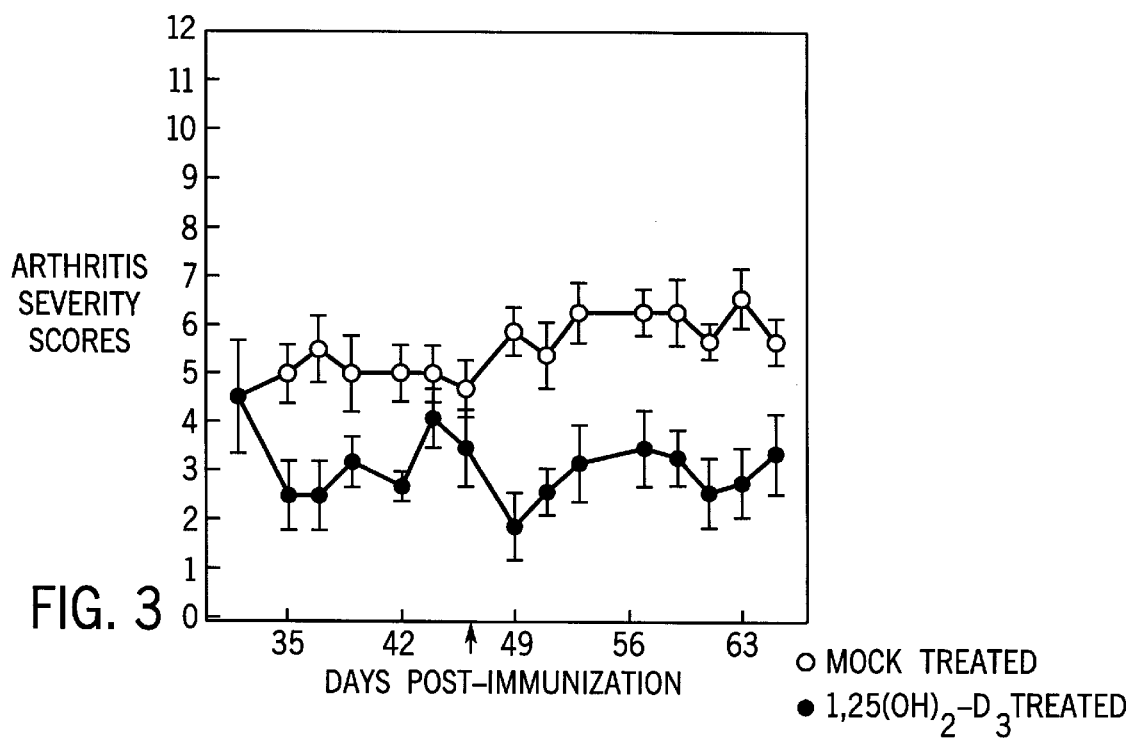
FIG. 3 is a graph of arthritis severity of mock-treated and 1,25-(OH)$_2$D$_3$-treated DBA/1 mice versus days post-treatment.

We then examined the relationship between $1,25(OH)_2D_3$-treatment and established arthritis. FIG. 3 graphs the results of an experiment in which mock-treated and $1,25(OH)_2D_3$-treated mice were compared in terms of their arthritis severity as a function of days post-treatment with $1,25(OH)_2$ vitamin $D_3$.

20 DBA/1 mice were started on an experimental diet which did not contain additional D and was low in calcium on day 14 post-immunization. As mice became arthritic (one of four paws was scored as 2 or higher) the mice were divided in two groups and treated with an intraperitoneal injection of 300 ng of $1,25-(OH)_2D_3$ in 0.1 ml of saline or mock injection (equivalent amount of ethanol in saline). Because all the mice did not develop arthritis at the same time, values from day 32 to day 45 reflect fewer than 10 mice/group. By day 49 post-immunization all the mice were treated and there were 10 mice/group. At the time of treatment the diet was also changed to contain 50 ng of $1,25-(OH)_2D_3$ and 0.2% $CaCO_3$ or no additional D and 0.2% $CaCO_3$. The paw scores per mouse were added and divided by the number of mice per treatment group and the standard error of the mean for 10 mice per group was calculated. The normally distributed group variances were compared using the Student's t test; $p<0.05$ was considered significant. By day 45 post-immunization the arthritis severity scores were significantly lower ($p<0.02$ or less) in $1,25(OH)_2D_3$-treated mice than controls.

FIG. 3 demonstrates that the mice treated with $1,25-(OH)_2D_3$ had a reduction in arthritis severity compared to the mock-treated mice. After 50 days (FIGS. 1 and 2) or 32 days (FIG. 3) on diets which contained 50 ng/day of $1,25(OH)_2D_3$ and 0.2% $CaCO_3$, serum calcium values were normal. Controls (no additional D)—7.8±0.1 mg %; $1,25(OH)_2D_3$ from day 14—7.7±0.1 mg %; $1,25(OH)_2D_3$ from day 32 to day 45—7.6±0.1 mg %.

We next evaluated the response of Lyme arthritis to $1,25-(OH)_2D_3$ treatment. As described above in Materials and Methods, 5 week old mice were injected intradermally on the back with *B. burgdorferi* and arthritis was quantitated by measuring changes in the ankle joint and foot pads of ether anesthetized mice. FIG. 4 graphs Lyme arthritis in $1,25-(OH)_2D_3$-treated (●) and control (○) treated mice. For these experiments all mice were fed 2.2% $CaCO_3$. The experimental diet provided 20 ng/day/mouse $1,25-(OH)_2D_3$ or no additional D and the diet was started on day before infection.

After three weeks on the experimental diets, the serum calcium values were 10.0±0.6 and 11.3±2.0 mg % in the controls and 1,25-(OH)$_2$D$_3$-treated mice respectively. Uninfected paw measurements were done the day before infection. Paw measurements on anesthetized animals (8-12/group, 2 paw/mouse) were made with an engineer's caliper. Values are mean ± SE 16–18 paws. The normally-distributed group variances were compared using the Student's t test; ρ>0.05 was considered significant. Referring to FIG. 4, * indicates significantly different, ρ≦0.0001 and + indicates significantly different, ρ≦0.01.

FIG. 4 demonstrates that the ankle and foot pad size is diminished in the 1,25-(OH)$_2$D$_3$-treated mice versus the mice receiving no vitamin D treatment.

We claim:

1. A method of treating rheumatoid arthritis or arthritis symptoms induced by infectious agents of an arthritis patient comprising the steps of
administering to a rheumatoid arthritis patient or a patient suffering from arthritis symptoms induced by infectious agents an amount of the following compound effective to reduce arthritis symptoms:

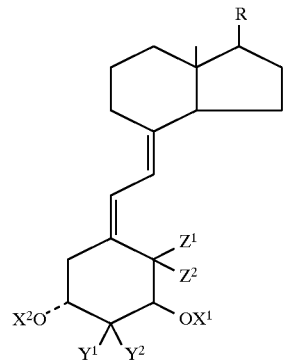

wherein $X^1$ and $X^2$ are each selected from the group consisting of hydrogen and acyl;
wherein $Y^1$ and $Y^2$ can be H, or one can be 0=arkyl or 0=alkyl and can have a β or α configuration; $Z^1$=$Z^2$=H or $Z^1$ and $Z^2$ together are CH$_2$; and
wherein R is an alkyl, hydroxyalkyl or fluoroalkyl group, or R may represent the following side chain:

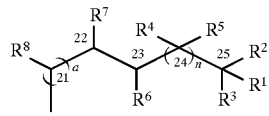

wherein (a) may have an S or R configuration, $R^1$ represents hydrogen, hydroxy or O-acyl, $R^2$ and $R^3$ are each selected from the group consisting of alkyl, hydroxyalkyl and fluoralkyl, or, when taken together represent the group-(CH$_2$),-wherein m is an integer having a value of from 2 to 5, R4 is selected from the group consisting of hydrogen, hydroxy, fluorine, O-acyl, alkyl, hydroxyalkyl and fluoralkyl, wherein if $R^5$ is hydroxyl or fluoro, $R^4$ must be hydrogen or alkyl, $R^5$ is selected from the group consisting of hydrogen, hydroxy, fluorine, alkyl, hydroxyalkyl and fluoroalkyl, or $R^4$ and $R^5$ taken together represent double-bonded oxygen, $R^6$ and $R^7$ taken together form a carbon-carbon double bond, $R^8$ may be H or CH$_3$, and wherein n is an integer having a value of from 1 to 5, and wherein the carbon at any one of positions 20, 22, or 23 in the side chain may be replaced by an O, S, or N atom.

2. The method of claim 1 wherein the compound is 1,25(OH)$_2$D$_3$.

3. The method of claim 2 wherein the amount of vitamin D analog administered is between 0.5 and 10 μg per day per 160 pound patient.

4. The method of claim 3 wherein the amount of vitamin D analog administered is between 0.5 and 0.75 μg per day per 160 pound patient.

5. The method of claim 3 wherein the amount of vitamin D analog administered is between 0.5 and 1.5 μg per day per 160 pound person.

6. The method of claim 1 wherein the symptom is joint swelling.

7. The method of claim 1 wherein the compound is selected from the group of 1,25-dihydroxyvitamin D$_3$, 19-nor-1,25-dihydroxyvitamin D$_2$, 19-nor-21-epi-1,25-dihydroxyvitamin D$_3$, 1,25-dihydroxy-24-homo-22-dehydro-22E vitamin D$_3$, and 19-nor-1,25-dihydroxy-24-homo-22-dehydro-22E-vitamin D$_3$.

8. The method of claim 1 wherein the amount of compound administered is between 0.5 and 10 μg per day per 160 pound patient.

9. The method of claim 1 wherein the amount of compound administered is between 0.5 and 0.75 μg per day per 160 pound patient.

10. The method of claim 1 wherein the amount of compound administered is between 0.5 and 1.5 μg per day per 160 pound patient.

11. The method of claim 1 wherein the dose is given orally.

12. The method of claim 1 wherein the patient is on a low calcium diet.

13. The method of claim 1 wherein the administering is at night.

14. The method of claim 1, wherein the dose is given orally and wherein the patient is on a low-calcium diet and wherein the dose is 0.5–3.0 μg 1,25-dihydroxyvitamin D$_3$/day or its analog equivalent.

* * * * *

UNITED STATES PATENT AND TRADEMARK OFFICE
CERTIFICATE OF CORRECTION

PATENT NO. : 5,891,865
DATED : April 6, 1999
INVENTOR(S) : Hector F. Deluca, et. al.

It is certified that error appears in the above-indentified patent and that said Letters Patent is hereby corrected as shown below:

Title page, item [54] and col. 1, the title should read --TREATMENT OF RHEUMATOID ARTHRITIC DISEASE AND ARTHRITIC DISEASE INDUCED BY INFECTIOUS AGENTS--.

Column 4, Line 14:
"≤" should be --≥--

Column 4, Line 23:
"≤" should be --≥--

Column 4, Line 24:
"≤" should be --≥--

Column 8, Line 16:
"≤" should be --≥--

Column 8, Line 17:
"≤" should be --≥--

Column 8, Line 18:
"≤" should be --≥--

Column 8, Line 25:
"≤" should be --≥--

Signed and Sealed this

Nineteenth Day of October, 1999

Attest:

Q. TODD DICKINSON

*Attesting Officer*        *Acting Commissioner of Patents and Trademarks*